United States Patent [19]

Scherrer

[11] 4,154,847

[45] May 15, 1979

[54] DERIVATIVES OF 2-NITRO-3-PHENYLBENZOFURANCARBOXALDEHYDES

[75] Inventor: Robert A. Scherrer, White Bear Lake, Minn.

[73] Assignee: Riker Laboratories, Inc., Northridge, Calif.

[21] Appl. No.: 919,414

[22] Filed: Jun. 26, 1978

[51] Int. Cl.$^2$ ............................................. C07D 31/345
[52] U.S. Cl. ..................................... 424/285; 542/408; 260/346.73; 260/346.22
[58] Field of Search .................... 260/346.73; 542/408; 424/285

[56] References Cited

U.S. PATENT DOCUMENTS

| | | | |
|---|---|---|---|
| 4,048,323 | 9/1977 | Scherrer | 260/346.22 |
| 4,066,782 | 1/1978 | Scherrer | 260/346.22 |
| 4,067,993 | 1/1978 | Scherrer | 260/346.22 |

FOREIGN PATENT DOCUMENTS

| | | |
|---|---|---|
| 846502 | 3/1977 | Belgium. |
| 2642877 | 4/1977 | Fed. Rep. of Germany. |

*Primary Examiner*—Natalie Trousof
*Assistant Examiner*—Bernard I. Dentz
*Attorney, Agent, or Firm*—Cruzan Alexander; Donald M. Sell; Donald C. Gipple

[57] ABSTRACT

Reaction products of 2-nitro-3-phenylbenzofurancarboxaldehydes with hydroxylamine, semicarbazide and benzoylhydrazine which are active as antimicrobial agents and processes for their use.

5 Claims, No Drawings

DERIVATIVES OF 2-NITRO-3-PHENYLBENZOFURANCARBOX- ALDEHYDES

BACKGROUND OF THE INVENTION

This invention relates to compounds produced by the reaction of 2-nitro-3-phenylbenzofurancarboxaldehydes with hydroxylamine, semicarbazide or phenylhydrazine and to the use of these compounds as antimicrobial agents.

2-Nitro-3-phenylbenzofurans substituted by acidic groups are known as are 2-nitro-3-phenylbenzofurans substituted by aldehyde groups (e.g. see U.S. Pat. Nos. 4,048,323; 4,066,782 and 4,067,993; Belgian Patent No. 846,502 and German Offenlegungsschrift No. P 2,642,877). It has now been found that when 2-nitro-3-phenylbenzofuran-type compounds substituted by aldehyde groups are reacted with certain —NH2 group-containing reagents, novel products are formed which are active antimicrobial agents.

DETAILED DESCRIPTION OF THE INVENTION

The present invention related to compounds of the formula:

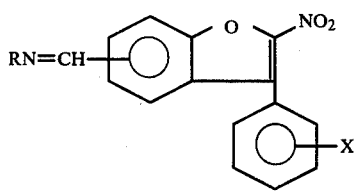

wherein R is HO—,

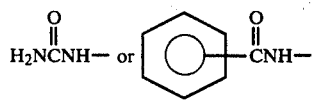

and X is hydrogen, halogen, methyl or methoxy. It also relates to the use of the compounds of formula I as antimicrobial agents. Halogen in formula I indicates fluorine, chlorine and bromine only.

The pure compounds of the invention are generally white or yellowish crystalline materials when purified. They are substantially insoluble in water or aliphatic hyrdrocarbons and are more soluble in lower alcohols, halogenated solvents, acetone, N,N-dimethylformamide and the like.

All of the compounds of the invention are active against bacteria and some are also active against other microorganisms, including fungi and protozoa, in vitro and topically. Thus, they can be used for disinfecting and sterilizing, for example of medical and dental equipment, as components of disinfecting solutions. The compounds are particularly useful and antibacterial agents.

Compounds of the invention which are presently preferred are those wherin X is hydrogen. Compounds of the invention wherein RN=CH— is substituted in the 5, 6 or 7 position are also presently preferred.

The compounds of the invention are conveniently prepared from starting materials known to the art or from intermediates prepared by methods well known to the art according to the following reaction:

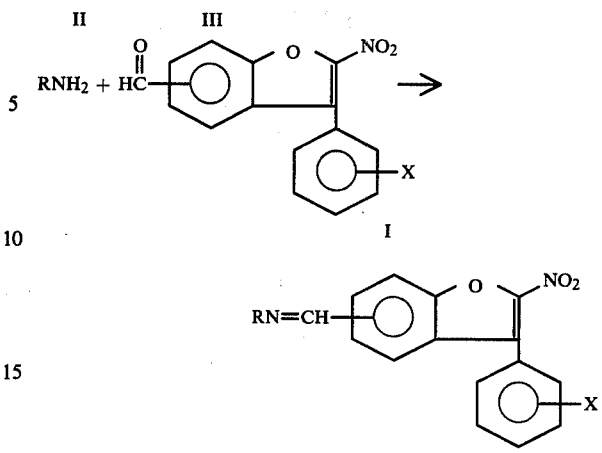

wherein R and X are as previously indicated. The compounds II (hydroxylamine, semicarbazide, both ordinarily used as the hydrochlorides, and benzoylhydrazine) are all known. The 2-nitro-3-phenylbenzofurancarboxaldehydes, III, are known as a class (e.g. see Belgian Patent 846,502) and the individual compounds are known specifically or they can be easily prepared by known methods.

To prepare the compounds I in which R is OH, hydroxylamine is reacted with the 2-nitro-3-phenylbenzofurancarboxaldehyde in a suitable non-reactive solvent such as ethanol by refluxing the hydrochloride in the presence of an acid acceptor such as sodium acetate.

To prepare the compounds I in which R is

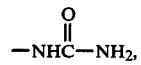

semicarbazide is reacted with the 2-nitro-3-phenylbenzofurancarboxaldehyde in a suitable non-reactive solvent such as ethanol by refluxing the hydrochloride in the presence of an acid acceptor such as sodium acetate.

To prepare the compounds I in which R is

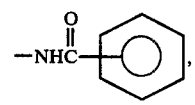

benzoylhydrazine and the 2-nitro-3-phenylbenzofurancarboxaldehyde are refluxed together in a suitable non-reactive solvent such as ethanol in the presence of an acid catalyst.

The antimicrobial activity of the compounds is evaluated using a variation of the original agar-plate diffusion method of Vincent and Vincent (e.g. see Vincent, J. G., and Vincent, Helen W., Proc. Soc. Exptl. Biol. Med. 55:162–164, 1944, and Davis, B. D., and Mingioli, E. S., J. Bac. 66:129–136, 1953). Using this test, the compounds of the invention have been found to have a broad spectrum of activity against both gram-positive and gram-negative microorganisms. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are: *Staphylococcus aureas, Bacillus subtilus, Pseudomonas aeruginosa, escherichi coli,*

Streptococcus sp. (strains isolated from dental carries in rats or hamsters at the National Institute of Dental Health and grown in PFY or APT agar), *Asperigillus niger, Candida albicans, Mima polymorpha, Herellea vaginicola, Klebsiella pneumoniae* and *Streptococcus fecaelis.*

These are selected representatives of various bacterial and fungal classes and broad spectrum activity can be predicted as a result of activity against them. All of the compounds of the invention possess antimicrobial activity towards one or more of them. The compounds maintain high activity against the microorganisms either in the absence or presence of 10 percent horse serum.

The in vivo antimicrobial activity is determined against infections produced by *Streptococcus pyogenes* C-203, and *Staphylococcus aureus* (Smith) or other bacterial species. The species used is determined by the in vitro antimicrobial spectrum of the compound. Groups of 5 or 10 mice, 18–22 g., are infected intraperitoneally with the test culture. Treatment consists of three oral injections one, six and 24 hours after infection. All mice are observed for extended periods, e.g. for two weeks, and deaths recorded at daily intervals. Control groups consist of one infected, nontreated group and other infected groups receiving varying dosages of a reference standard.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing the object to be treated therein, or by local application to an infected area. The amount of compound to be used for treatment of a microbial infection will be an effective amount less than a toxic amount. The amount to be administered to a subject and route of administration to control an infection will depend on the species of organism, the sex, weight, physical condition of the subject, the locus of the infection, and many other factors, but this judgment is well within the skill of the art. Usually the amount will be less than 100 mg/kg per dose. Conveniently the oral treatment is administered in the form of the usual pharmaceutical preparations such as capsules, tablets, emulsions, solutions, suppositories and the like. Excipients, fillers, coatings, etc., are employed with tablets or capsules, as is well known in the art.

It is often advantageous to combine the compounds of this invention with other antimicrobial compounds such as coccidiostats, anthelmintics, antifungals, antibiotics, steroids, or antibacterial agents, or to combine more than one compound described herein in a single composition.

In view of the outstanding antimicrobial activity of the compounds of the invention they would also be expected to be effective growth promoters in various animal and bird species.

The following examples are given for the purpose of illustrating some of the synthetic methods useful in the invention, but are not intended to limit the invention. The melting points are uncorrected and the temperatures are in degrees Centigrade.

EXAMPLE 1

To a mixture of 2.7 g. (0.01 mole) of 2-nitro-3-phenylbenzofuran-7-carboxaldehyde in 20 ml. of ethanol is added 1.1 g. (0.016 mole) of hydroxylamine hydrochloride and 1.4 g. (0.017 mole) of sodium acetate in 20 ml. of ethanol. The solution is heated at its reflux temperature for about 15 minutes, then an additional 20 ml. of ethanol is added. Refluxing is continued for a total of 2 hours, then the mixture is allowed to sit at about 20° C. for about 16 hours. The product is separated by filtration, washed with ethanol, then with water, then recrystallized twice from trichloroethylene. The product is yellow crystals of 2-nitro-3-phenylbenzofuran-7-aldoxime, m.p. 218.5°–219° C.

| Analysis: | % C | % H | % N |
|---|---|---|---|
| Calculated for $C_{15}H_{10}N_2O_4$: | 63.8; | 3.6; | 9.9 |
| Found: | 63.4; | 3.5; | 10.0. |

EXAMPLE 2

To a mixture of 2.1 g. (0.0079 mole) of 2-nitro-3-phenylbenzofuran-7-carboxaldehyde in 70 ml. of ethanol is added 1.34 g. (0.012 mole) of semicarbazide hydrochloride and 1.07 g. (0.013 mole) of sodium acetate. The mixture is heated to its reflux temperature and maintained at reflux for 3 hours. The precipitated product is separated by filtration, washed with water and diethyl ether. The solid is washed with hot dichloroethane, separated by filtration, then dissolved in a mixture of 650 ml. of chloroform and 100 ml. of acetone by heating. This solution is washed twice with water, once with sodium bicarbonate solution, again with water, once with dilute hydrochloric acid, and twice with water. The solution is dried and the dry solution is evaporated to provide solid 2-nitro-3-phenylbenzofuran-7-carboxaldehyde semicarbazone, m.p. 249° C. (dec.).

| Analysis: | % C | % H | % N |
|---|---|---|---|
| Calculated for $C_{16}H_{12}N_4O_4$: | 59.2; | 3.7; | 17.3 |
| Found: | 58.4; | 3.9; | 17.3. |

EXAMPLE 3

A mixture of 3 g. (0.0112 mole) of 2-nitro-3-phenylbenzofuran-7-carboxaldehyde, 1.53 g. (0.0112 mole) of benzoylhydrazine and 0.8 ml. of acetic acid in 150 ml. of ethanol is stirred at 20° C. for 24 hours. The yellow solid is separated by filtration, washed with ethanol, then with diethyl ether and recrystallized three times from dichloroethane, then from acetic acid to provide yellow solid 1-benzoyl-2-(2-nitro-3-phenyl-7-benzofuranylidene)hydrazine, m.p. 246.5°–248° C.

| Analysis: | % C | % H | % N |
|---|---|---|---|
| Calculated for $C_{22}H_{15}N_3O_4$: | 68.6; | 3.9; | 10.9 |
| Found: | 68.3; | 4.1; | 11.1. |

Using the methods described in Examples 1, 2 and 3, the compounds of the invention shown in Tables I, II and III are prepared. The individual 3-phenylbenzofurancarboxaldehydes are known or are prepared from the known phenols and α-bromoacetophenones by methods known to the art.

TABLE I
| Example No. | Aldehyde Intermediate | Product |
|---|---|---|
| 4 | 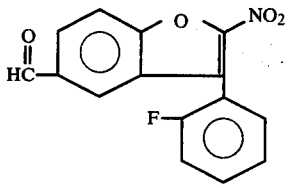 | 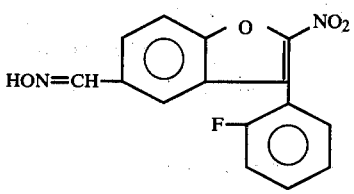 |
| 5 | 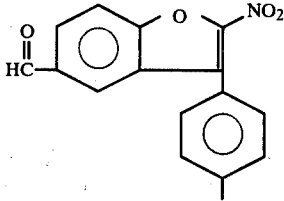 | 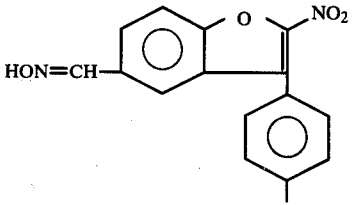 |
| 6 | 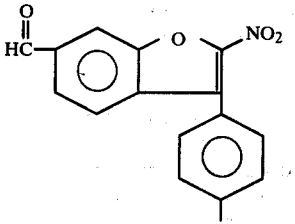 | 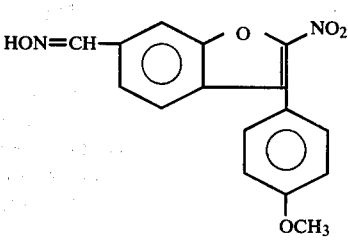 |
TABLE II
| Example No. | Aldehyde Intermediate | Product |
|---|---|---|
| 7 | 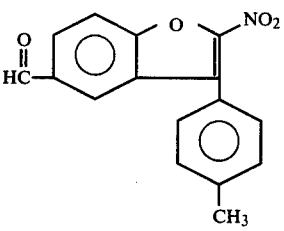 | 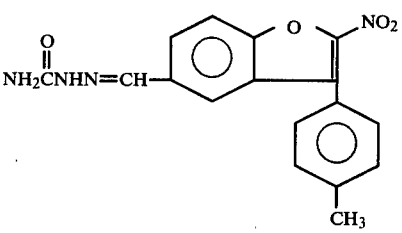 |
| 8 | 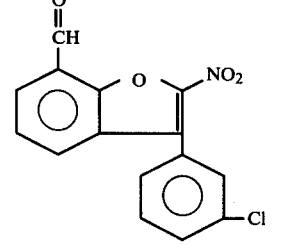 | 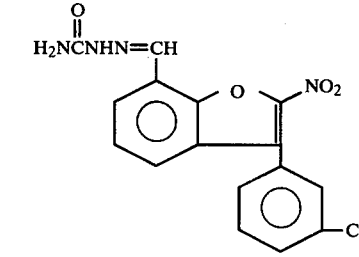 |
TABLE III
| Example No. | Aldehyde Intermediate | Product |
|---|---|---|
| 9 | 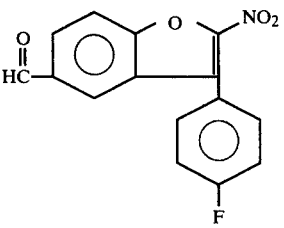 | 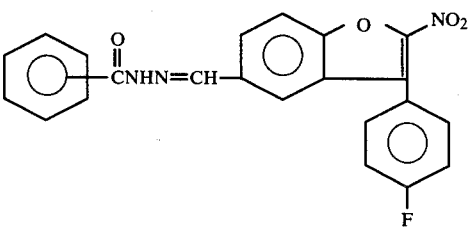 |

TABLE III-continued

| Example No. | Aldehyde Intermediate | Product |
|---|---|---|
| 10 | 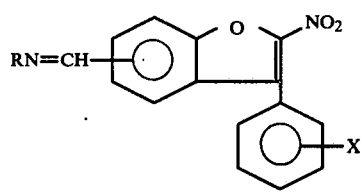 | 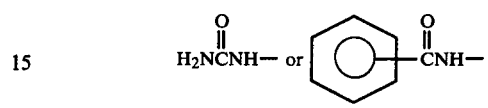 |

What is claimed is:
1. A compound of the formula

RN=CH—[benzofuran with O, NO2, phenyl-X substituents]

wherein R is HO—, $$H_2N\overset{O}{\overset{\|}{C}}NH- \text{ or } \phenyl-\overset{O}{\overset{\|}{C}}NH-$$

and X is hydrogen, halogen, methyl or methoxy.

2. The compound 2-nitro-3-phenylbenzofuran-7-aldoxime according to claim 1.

3. The compound 2-nitro-3-phenylbenzofuran-7-carboxaldehyde semicarbazone according to claim 1.

4. The compound 1-benzoyl-2-(2-nitro-3-phenyl-7-benzofuranylidene)hydrazine according to claim 1.

5. A method for arresting or inhibiting the growth of bacteria comprising contacting said bacteria with a compound according to claim 1 in an amount sufficient to inhibit the growth of said bacteria.

* * * * *